US00PP09703P

United States Patent [19]

Rotolante

[11] Patent Number: Plant 9,703

[45] Date of Patent: Nov. 19, 1996

[54] ANTHURIUM 'ROTOLANTE NUMBER 3'

[75] Inventor: Denis W. Rotolante, Homestead, Fla.

[73] Assignee: Agri-Starts Inc., Apopka, Fla.

[21] Appl. No.: 402,853

[22] Filed: Mar. 13, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 8,129 2/1993 Georgusis ..... Plt./88.1

*Primary Examiner*—James R. Feyrer

*Attorney, Agent, or Firm*—Frank B. Robb; Robb & Robb

[57] ABSTRACT

An Anthurium cultivar of vigorous growth, continuously and profusely producing blooms from white buds with petals having a front of white with pink blush centers and a back of white. The blooms retain their color as the plant matures. The bloom is very long lasting both on the plant and as a cut flower and exhibits no discoloration until at least four weeks from cutting.

1 Drawing Sheet

GENERAL DESCRIPTION OF THE INVENTION

There is disclosed a new Anthurium plant of the *Anthurium andreanum* species resulting from a definite effort to produce an improvement in the species.

I discovered my new Anthurium plant by cross breeding the seed of the Anthurium known as 'Antioquiensis', unpatented, with the pollen of the Anthurium known as 'Cultorum Straight White', unpatented, neither publicly available, in an aspect sterile laboratory environment in a nursery located near Apopka, Fla.

In the nursery, we produce substantial quantities of Anthurium and I have crossed certain varieties in an effort to produce new cultivars of varying forms, colors and characteristics.

The plant of this disclosure was the result of such effort. This seedling was grown to maturity with siblings, retained for evaluation and testing and was selected when found to produce highly desirable specimen plants when potted and to produce flowers in good quantity and suitable character for cutting for the florist industry. The spathe color of this plant was noted to be an unusual light red-purple complimenting the white spadix. Flowers were found to have exceptional lasting quality whether left to mature on the plant or when taken as a cut flower. The strength of the long peduncle with the sizes, shapes and attitudes of the spathe and spadix make this plant ideally suited for the production of cut flowers of the highest quality.

I have caused my new plant to be asexually reproduced by tissue culture, and find that it comes true in successive generations which have been produced over time.

As will be understood from a consideration of the drawing, my new plant has some outstanding differences from known varieties. In particular, it is a vigorously growing plant, continuously and profusely producing blooms from white buds. The spathes have a upper of white with pink blush centers and a lower of white. The blooms retain their color as the plant matures. The bloom is very long lasting both on the plant and as a cut flower and exhibits no discoloration until at least four weeks from cutting.

Thus I have disclosed unique characteristics which present a very different appearance from other Anthurium varieties or cultivars with which I am familiar.

Detailed characteristics of my plant are set forth hereinafter and where color is referred to as before and hereafter, The Royal Horticultural Society Colour Chart is used as a basis for comparison with the illustrations made by photographic process which is as nearly true as possible to make by such means. It is particularly difficult to obtain illustrations of the darker colors displayed, but those shown are nearly true as can be supplied.

BOTANICAL DESCRIPTION OF THE PLANT

Figure 1:
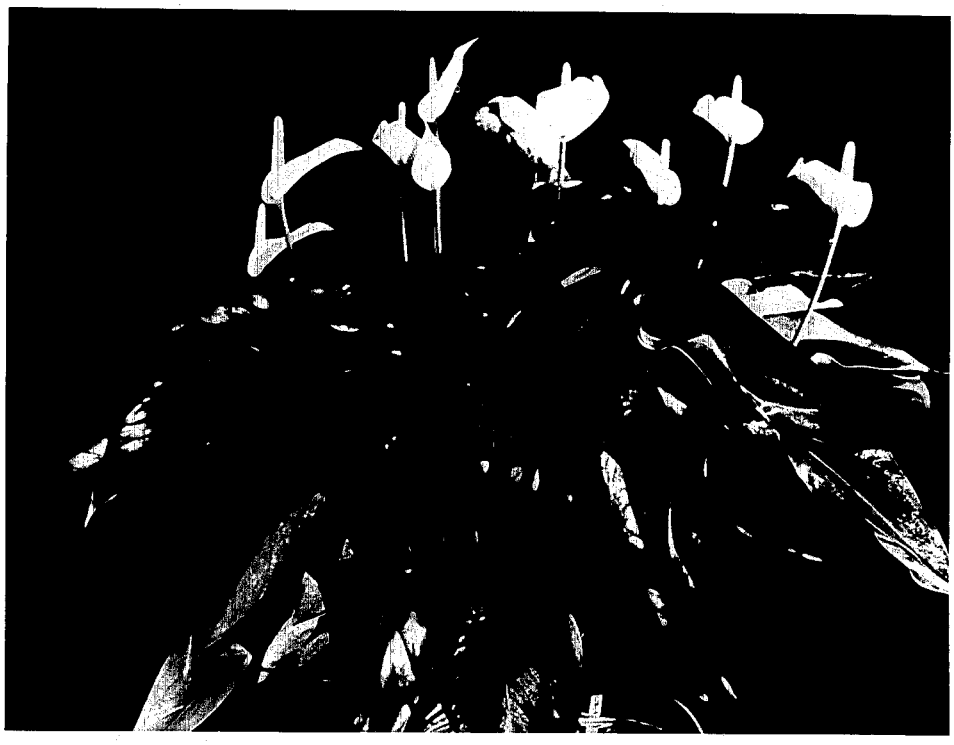
FIG. 1 of the drawing depicts, in side view, a profile of a mature specimen the plant showing leaves in all maturity stages, and the character and degree of inflorescence. The spathe and spadix of flowers of various stages of maturity are shown in a number typical for this plant. Typical attitudes for the leaf petioles, the peduncles, spathes and spadices are shown, as are both the top and bottom leaf surfaces. The characteristic involute aspect of both leaves and spathes is also illustrated.
Figure 2:
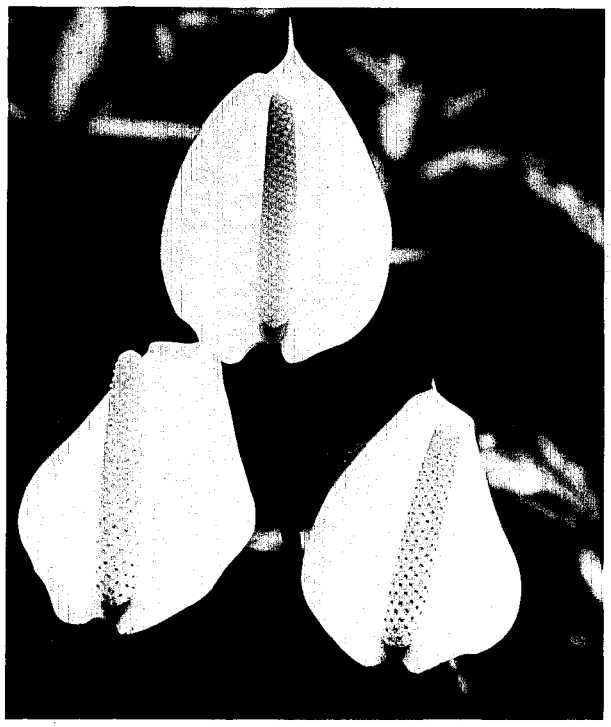
FIG. 2 is a close-up of three flowers of differing stages of maturity which shows the details of subtle coloration of spadices, the coloration of spathes and the characteristic shape of the spathes produced by this plant.

Parentage:

*Seed parent.*—*Anthurium andreanum* 'Antioquiensis', unpatented.

*Pollen parent.*—*Anthurium andreanum* 'Cultorum Straight white' unpatented.

Propagation: Plant tissue culture near Apopka, Fla.

Classification: *Anthurium andreanum* hybrid.

Plant description:

*Stem.*—Strong of medium size.

*Petioles.*—23–30 cm. Color green (146 A).

*Leaves.*—Medium size: 20–28 cm. long by 14–18 cm. wide, generally lanceloate with the basal portions varying between truncate and obtuse, abundant, smooth texture and smooth edges, the upper side is smooth and green color (darker than 131 A), the under side is smooth and green color (146 B), medium length, smooth stipules and ordinary ribs and veins.

*Bud.*—Medium size: 5–7 cm. long, pointed, white color (69 A); opening well and not affected by wet or hot weather.

*Flower.*—Type: Spathe and Spadix. Borne singly Spathe: The Spathe is cupped upon first opening and then flattens and is shiny inside and outside with no pubescence; Medium size: 5–6.5 cm. wide by 6–10 cm. long. Form — Oval and pointed. Color — Upper: White (69 A) with pink blush (65 D) in the center. Lower: White (155 D). Texture — Thick and leathery.

*Peduncle.*—Medium size: 35–45 cm. long by 4–5 mm. diameter. Green color (146 C). Smooth, stiff and nested in foliage and is not affected by adverse conditions.

Reproductive organs:

*Spadix.*—4–6 cm. long by 6–9 mm. wide., color: base white (69 D), middle (37 B), tip (2 C).

*Flowering time.*—Continuous, once reaching blooming size wich takes seven months from a 10 cm. tissue culture plug, under proper growing conditions.

*Disease.*—Initial greenhouse trials near Apopka, Fla. indicate good resistance against traditional diseases.

*Insects.*—No unusual susceptibility to insects noted to date.

GENERAL OBSERVATIONS

The plant has no fragrance and grows as a bush exhibiting vigorous, compact growth with a height of 18–22 in. and a spread of 36 in. in a 10 in. pot.

I claim:

1. A new and distinct Anthurium plant substantially as herein shown and described, characterized particularly as to novelty by its vigorous growth, continuously and profusely producing blooms from white buds and with spathes having a front of white with pink blush centers and a back of white said petals being very long lasting and retaining their color as the plant matures.

* * * * *